(12) United States Patent
Corvari et al.

(10) Patent No.: US 7,229,644 B2
(45) Date of Patent: Jun. 12, 2007

(54) PHARMACEUTICAL FORMULATIONS OF MODAFINIL

(75) Inventors: Vincent Corvari, Carmel, IN (US); George Grandolfi, Milford, OH (US); Alpa Parikh, Hockessin, DE (US)

(73) Assignee: Cephalon, Inc., Frazer, PA (US)

( * ) Notice: Subject to any disclaimer, the term of this patent is extended or adjusted under 35 U.S.C. 154(b) by 335 days.

(21) Appl. No.: 10/243,557

(22) Filed: Sep. 13, 2002

(65) Prior Publication Data

US 2003/0220403 A1    Nov. 27, 2003

Related U.S. Application Data

(63) Continuation-in-part of application No. 10/155,913, filed on May 23, 2002.

(51) Int. Cl.
*A61K 9/14* (2006.01)

(52) U.S. Cl. .................... 424/488; 424/464; 424/469; 424/470; 514/211

(58) Field of Classification Search ............... 424/464, 424/458, 434, 424, 423, 426, 465–490; 514/11, 514/211, 221, 618; 512/11, 211, 221
See application file for complete search history.

(56) References Cited

U.S. PATENT DOCUMENTS

| | | | |
|---|---|---|---|
| 1,570,994 A | | 1/1926 | Cook |
| 4,177,290 A | | 12/1979 | Lafon |
| 4,748,023 A | * | 5/1988 | Tamas et al. ............... 424/465 |
| 4,927,855 A | * | 5/1990 | Lafon .......................... 514/618 |
| 5,180,745 A | | 1/1993 | Lafon |
| 5,391,576 A | * | 2/1995 | Lafon .......................... 514/618 |
| 5,401,776 A | | 3/1995 | Laurent |
| 5,569,654 A | * | 10/1996 | Armour et al. ............. 514/221 |
| 5,612,379 A | | 3/1997 | Laurent |
| 5,618,845 A | | 4/1997 | Grebow et al. |
| 5,843,347 A | | 12/1998 | Nguyen et al. |
| 5,948,437 A | * | 9/1999 | Parikh et al. ............... 424/464 |
| 6,042,847 A | * | 3/2000 | Kerc et al. .................. 424/472 |
| 6,204,245 B1 | * | 3/2001 | Siegel et al. ................ 514/11 |
| 6,248,363 B1 | | 6/2001 | Patel et al. |
| 6,267,985 B1 | | 7/2001 | Chen et al. |
| 6,294,192 B1 | | 9/2001 | Patel et al. |
| 6,346,548 B1 | * | 2/2002 | Miller et al. ................ 514/618 |
| 6,451,339 B2 | | 9/2002 | Patel et al. |
| 6,455,588 B1 | * | 9/2002 | Scammell et al. .......... 514/618 |
| 6,488,164 B2 | | 12/2002 | Miller et al. |
| 6,492,396 B2 | | 12/2002 | Bacon et al. |
| 6,569,463 B2 | | 5/2003 | Patel et al. |
| 6,670,358 B2 | | 12/2003 | Bacon et al. |
| 2001/0034373 A1 | | 10/2001 | Miller et al. |
| 2003/0022940 A1 | | 1/2003 | Corvari et al. |
| 2003/0077297 A1 | | 4/2003 | Chen et al. |
| 2003/0104048 A1 | | 6/2003 | Patel et al. |
| 2003/0171439 A1 | | 9/2003 | Lawyer et al. |

FOREIGN PATENT DOCUMENTS

| | | |
|---|---|---|
| FR | 2702968 | 9/1994 |
| WO | WO 94/21371 | 9/1994 |
| WO | WO 99/12524 A1 * | 3/1999 |
| WO | WO 00/37055 | 6/2000 |
| WO | WO 01/13906 | 3/2001 |
| WO | WO 02/30414 | 4/2002 |
| WO | WO 02/096401 | 12/2002 |
| WO | WO 03/068186 | 8/2003 |
| WO | WO 2004/004692 | 1/2004 |
| WO | WO 2004/010979 | 2/2004 |

OTHER PUBLICATIONS

Cephalon, "Provigil-TM (modafinil) Tablets", FDA Approved Labeling Dec. 1998, Retrieved from the Internet: URL:http://www.fda.gov/cder/foi/label/1998/207171b1.pdf, retrieved on Oct. 29, 2003, p. 1 & 10.
Edgar et al., "Modafinil Induces Wakefulness Without Intensifying Motor Activity or Subsequent Rebound Hypersomnolence in the Rat", Journal of Pharmacology and Experimental Therapeutics, vol. 283 (2), 1997, p. 757-769.
Rudnick et al., Gennaro publisher, "Remington: The Science and Practice of Pharmacy", 1995, Mack Publishing Company, Easton, PA, pp. 1615-1620.
Hermant et al., "Awakening properties of modafinil: effect on nocturnal activity in monkeys (Macaca mulatta) after acute and repeated administration.", Psychopharmacology (Berl), 103(1), 1991, pp. 28-32.
Kibbe, "Handbook of Pharmaceutical Excipients", 3$^{rd}$ Edition, 2000, American Pharmaceutical Association, Pharmaceutical Press, Washington, DC, Sec. 7, pp. 305, 276, 102, 528, 87, 433.
Lin et al., "Role of catecholamines in the modafinil and amphetamine induced wakefulness, a comparative pharmacological study in the cat.", Brain Res,. 591 (1992), pp. 319-326.
Panckeri et al. "Modafinil decreases hypersomnolence in the English bulldog, a natural animal model of sleep-disordered breathing" Sleep, 19(8), 1996, pp. 626-631.
Shelton, et al., "Comparative effects of modafinil and amphetamine on daytime sleepiness and cataplexy of narcoleptic dogs", Sleep, 18(10), 1995, pp. 817-826.
Taylor et al., "Efficacy of modafinil compared to dextroamphetamine for the treatment of attention deficit hyperactivity disorder in adults", Journal of Child and Adolescent Psychopharmacology, vol. 10, No. 4, Jan. 2000, pp. 311-320.
Touret et al., "Awakening properties of modafinil without paradoxical sleep rebound: comparative study with amphetamine in the rat", Neuroscience Letters, 189, 1995, pp. 43-46.

* cited by examiner

*Primary Examiner*—Michael G. Hartley
*Assistant Examiner*—Micah-Paul Young

(57) ABSTRACT

The present invention is related to compositions of modafinil, including compositions of modafinil and one or more diluents, disintegrants, binders and lubricants, and the processes for their preparation thereof.

4 Claims, No Drawings

PHARMACEUTICAL FORMULATIONS OF MODAFINIL

This Application is a continuation-in-part of U.S. application, Ser. No. 10/155,913 filed May 23, 2002.

FIELD OF THE INVENTION

The present invention is related to compositions of modafinil and processes for the preparation thereof. The present invention relates to compositions that include modafinil and one or more diluents, disintegrants, binders and lubricants. The present invention further relates to processes for the preparing a solid dosage form of modafinil by wet mixing modafinil and excipients with water.

BACKGROUND OF THE INVENTION

Modafinil, $C_{15}H_{15}NO_2S$, also known as 2-(benzhydrylsulfinyl) acetamide, or 2-[(diphenylmethyl) sulfinyl] acetamide, is a synthetic acetamide derivative with wake-promoting activity, the structure of which has been described in French Patent No. 78 05 510 and in U.S. Pat. No. 4,177,290 ('290), and which has been approved by the United States Food and Drug Administration for use in the treatment of excessive daytime sleepiness associated with narcolepsy. Modafinil has been tested for treatment of several behavioral conditions in combination with various agents including apomorphine, amphetamine, reserpine, oxotremorine, hypnotics, yohimbine, 5-hydroxytryptophan, and monoamine oxidase inhibitors, as described in the cited patents. A method of preparation of a racemic mixture is described in the '290 patent and a method of preparation of a levorotatory isomer is described in U.S. Pat. No. 4,927,855 (both incorporated herein by reference). The levorotatory isomer is reported to be useful for treatment of hypersomnia, depression, Alzheimer's disease and to have activity towards the symptoms of dementia and loss of memory, especially in the elderly.

The primary pharmacological activity of modafinil is to promote wakefulness. Modafinil promotes wakefulness in rats (Touret et al., 1995; Edgar and Seidel, 1997), cats (Lin et al., 1992), canines (Shelton et al., 1995) and non-human primates (Hernant et al, 1991) as well as in models mimicking clinical situations, such as sleep apnea (English bulldog sleep disordered breathing model) (Panckeri et al, 1996) and narcolepsy (narcoleptic canine) (Shelton et al, 1995).

Modafinil has also been described as an agent with activity in the central nervous system, and as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). U.S. Pat. No. 5,618,845 describes modafinil preparations of a defined particle size less than about 200 microns. In addition, modafinil may be used in the treatment of eating disorders, or to promote weight gain or stimulate appetite in humans or animals (U.S. patent application Ser. No. 09/640,824, incorporated herein by reference), or in the treatment of attention deficit hyperactivity disorder (ADHD), or fatigue, especially fatigue associated with multiple sclerosis (U.S. Pat. No. 6,346,548, incorporated herein by reference).

Modafinil was known in the art in the form of a therapeutic package, marketed under the name Provigil®. Provigil® is a pharmaceutical product manufactured by Cephalon, Inc. of West Chester, Pa. and is also marketed by Cephalon, Inc. Provigil® is supplied as tablets containing 100 mg or 200 mg modafinil, with several excipients, including magnesium silicate and talc. In commercial use, modafinil-containing therapeutic packages in the prior art were labeled and otherwise indicated for use in narcolepsy patients.

It is desirable to optimize the formulation of a solid dose form of modafinil, and the methods of their preparation on a commercial scale. In particular, new formulations of modafinil have been discovered which exhibit comparable stability, dissolution rate, hardness, friability, thickness, disintegration, size and shape, and weight variation characteristics to that of Provigil®. Further, it has been discovered that solid dose forms of modafinil can be prepared, with properties similar to that of Provigil®, without inclusion of magnesium silicate or talc.

In addition, the newly discovered formulations preferably use a minimal number of excipients, and use pharmaceutical grade excipients that are inexpensive, readily available and that facilitate cost-effective manufacture on a commercial scale.

Furthermore, there is a need to improve upon the manufacturing process of the tablet form of modafinil. Improvement in the commercial preparation include minimizing the number of excipients, eliminating the use of organic solvents, reducing the number of steps, and reducing the time and expense of manufacture. The present invention is directed to these, as well as other, important ends.

SUMMARY OF THE INVENTION

The present invention relates to novel compositions of modafinil and the processes for their manufacture. In particular, modafinil is admixed with various excipients to formulate a solid dose of modafinil. In certain embodiments, the solid dose is in tablet form, in other embodiments, it is in capsule form.

An additional aspect of the present invention include processes for the preparation of modafinil formulations. In particular, the processes involve preparation of a solid dosage form of modafinil, preferably by wet mixing modafinil and excipients with water, followed by drying and milling of the granulated mixture.

Other aspects of the present invention include use of these compositions for the treatment of a disease or disorder in a subject in need thereof comprising administering to the subject a therapeutically effective amount of the compositions of the present invention.

DETAILED DESCRIPTION OF THE INVENTION

As used herein, "about" refers to a range of values ±10% of a specified value. For example, "about 20" includes ±10% of 20, or from 18 to 22.

As used herein, "modafinil" refers to modafinil, its racemic mixtures, individual isomers, acid addition salts, such as a metabolic acid of modafinil, benzhydrylsulfinylacetic acids, and its sulfone forms, hydroxylated forms, polymorphic forms, analogs, derivatives, cogeners and prodrugs thereof. Prodrugs are known in the art as compounds that are converted to the active agent (modafinil) in the body of a subject.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "subject" refers to a warm blooded animal such as a mammal, preferably a human or a human child, which is afflicted with, or has the potential to be afflicted with one or more diseases and conditions described herein.

As used herein, "therapeutically effective amount" refers to an amount which is effective in reducing, eliminating, treating, preventing or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, "unit dose" means a single dose which is capable of being administered to a subject, and which can be readily handled and packaged, remaining as a physically and chemically stable unit dose comprising either modafinil, or a pharmaceutically acceptable composition comprising modafinil.

In one embodiment, the present invention provides for compositions of modafinil without magnesium silicate or talc. Other embodiments include compositions of modafinil with one or more diluents, disintegrants, binders and lubricants. Preferably, the excipients meet the standards of the National Formulary ("NF") or United States Pharmacopoeia ("USP"). In a particular embodiment, there is provided a composition consisting of modafinil with one or more diluents, disintegrants, binders and lubricants.

In certain preferred embodiments, the composition comprises modafinil; one or more diluents, each independently chosen from a starch, a lactose monohydrate or a microcrystalline cellulose; one or more disintegrants, each independently chosen from a pregelatinized starch or a cross-linked sodium carboxymethyl cellulose; a binder; and a lubricant. In other preferred embodiments, the binder is a polyvinyl pyrrolidone, and the lubricant is magnesium stearate. In certain more preferred embodiments, a diluent is Fast Flo® #316, a second diluent is Avicel® PH 102; a disintegrant is Starch 1500®, a second disintegrant is Ac-Di-Sol®; and the binder is Povidone K-29/32. In other preferred embodiments, the diluent is Lactose Monohydrate, NF; the disintegrant is Croscarmellose Sodium, NF or Ac-Di-Sol®; and the binder is Povidone, USP.

The excipients are selected to ensure the delivery of a consistent amount of modafinil in a convenient unit dosage form and to optimize the cost, ease and reliability of the manufacturing process. All excipients must be inert, organoleptically acceptable, and compatible with modafinil. The excipients used in a solid oral formulation, commonly include fillers or diluents, binders, disintegrants, lubricants, antiadherents, glidants, wetting and surface active agents, colors and pigments, flavoring agents, sweeteners, adsorbents, and taste-maskers.

Diluents are typically added to a small amount of the active drug to increase the size of the tablet. The most common diluent is lactose, which exists in two isomeric forms, alpha-lactose or beta-lactose, and can be either crystalline or amorphous. Various types of lactose include spray dried lactose monohydrate (such as Super-Tab™), alpha-lactose monohydrate (such as Fast Flo®), anhydrous alpha-lactose, anhydrous beta-lactose, and agglomerated lactose. Other diluents include sugars, such as compressible sugar NF, dextrose excipient NF, and dextrates NF. A preferred diluent is lactose monohydrate (such as Fast Flo®). Other preferred diluents include microcrystalline cellulose (such as Avicel® PH, and Ceolus™), and microfine cellulose (such as Elcema®).

Diluents may include starch and starch derivatives. Starches include native starches obtained from wheat, corn, rice and potatoes. Other starches include pregelatinized starch NF, and sodium starch glycolate NF. Starches and starch derivatives also function as disintegrants. Other diluents include inorganic salts, such as dibasic calcium phosphate USP (such as Di-Tab® and Emcompress®), tribasic calcium phosphate NF (such as Tri-Tab® and Tri-Cafos®), and calcium sulfate NF (such as Compactrol®). Such polyols as mannitol USP, sorbitol NF, and xylitol NF may also serve as diluents. Many diluents also function as disintegrants and binders, and these additional properties must be taken into account when developing a formulation.

Disintegrants are included in tablet formulations to break the tablets into particles of the active pharmaceutical ingredient and excipients which will facilitate dissolution of the active ingredient and enhance bioavailability of the active ingredient. Starch and starch derivatives, including cross-linked sodium salt of a carboxymethyl ether of starch (such as sodium starch glycolate NF, Explotab®, and Primogel®) are useful disintegrants. A preferred disintegrant is pregelatinized starch, such as Starch 1500®. Another preferred disintegrant is cross-linked sodium carboxymethyl cellulose (such as Croscarmellose Sodium NF, Ac-Di-Sol®). Other disintegrants include cross-linked polyvinylpyrrolidone (such as Crospovidone NF), microcrystalline cellulose (such as Avicel® PH).

Binders are used as a wet granulation excipient to agglomerate the active pharmaceutical ingredient and the other excipients. A binder is selected to improve powder flow and to improve compactibility. Binders include cellulose derivatives such as microcrystalline cellulose NF, methylcellulose USP, carboxymethylcellulose sodium USP, hydroxypropyl methylcellulose USP, hydroxyethyl cellulose NF, and hydroxypropyl cellulose NF. Other binders include polyvidone, polyvinyl pyrrolidone, gelatin NF, natural gums (such as acacia, tragacanth, guar, and pectin), starch paste, pregelatinized starch NF, sucrose NF, corn syrup, polyethylene glycols, and sodium alginate, ammonium calcium alginate, magnesium aluminum silicate, polyethylene glycols. A preferred binder is polyvinyl pyrrolidone, in particular, Povidone USP, and preferably, povidone K-29/32.

Lubricants are used in tablet formulation to prevent sticking of the tablet to the punch faces and to reduce friction during the compression stages. Lubricants typically include vegetable oils (such as corn oil), mineral oils, polyethylene glycols (such as PEG-4000 and PEG-6000), salts of stearic acid (such as calcium stearate, magnesium stearate, and sodium stearyl fumarate), mineral salts (such as talc), inorganic salts (such as sodium chloride), organic salts (such as sodium benzoate, sodium acetate, and sodium oleate) and polyvinyl alcohols. A preferred lubricant is magnesium stearate.

Glidants are used in solid dose formulations to improve flow, generally by reducing interparticle friction. Commonly used glidants include microcrystalline cellulose (such as Avicel® PH, and Ceolus™), alkali stearates (such as magnesium stearate or calcium stearate), silicate salts (such as magnesium silicate, magnesium trisilicate, magnesium silicate anhydrous, calcium silicate), starches, mineral salts (such as talc), and colloidal silicon dioxide (such as Cab-O-Sil®, Syloid®, Aerosil®). Glidants can also function as diluents, lubricants, and hardening agents.

In other embodiments, modafinil comprises from about 30-50% by weight of the composition. Preferably, the composition comprises a diluent which is a lactose monohydrate, a second diluent which is a microcrystalline cellulose; a disintegrant which is a pregelatinized starch, a second disintegrant which is a cross-linked sodium carboxymethyl cellulose; a binder which is a polyvinyl pyrrolidone, and a lubricant which is magnesium stearate.

In certain other preferred embodiments, the lactose monohydrate is from about 25-40% of the composition by weight; the microcrystalline cellulose is from about 5-15%, the pregelatinized starch is from about 5-15%, the cross-linked sodium carboxymethyl cellulose is from about 1-10%, the polyvinyl pyrrolidone is from about 1-10%, and the magnesium stearate is from about 0.2-2.0%. In certain more preferred embodiments, the lactose monohydrate is Fast Flo® #316; the microcrystalline cellulose is Avicel® PH 102; the pregelatinized starch is Starch 1500®, the cross-linked sodium carboxymethyl cellulose is Ac-Di-Sol®; and the polyvinyl pyrrolidone is Povidone K-29/32.

In a particularly preferred embodiment, modafinil is about 40.0% of the composition by weight, Fast Flo®#316 is about 28.7%, the Avicel® PH 102 is about 10.4%, the Starch 1500® is about 10.9%, the Ac-Di-Sol® is about 4.0%, the Povidone K-29/32 is about 5.2% and the magnesium stearate is about 0.8%.

In other embodiments, modafinil comprises from about 70-80% of the composition by weight. Preferably the composition comprises a diluent, such as a lactose monohydrate, preferably from about 3-20% of the composition by weight; a disintegrant, such as a cross-linked sodium carboxymethyl cellulose, preferably from about 2-10% of the composition by weight; a binder such as a polyvinyl pyrrolidone, preferably from about 2-10% of the composition by weight; and a lubricant such as magnesium stearate, preferably from about 0.2-2.0% of the composition by weight. In certain more preferred embodiments, the diluent is Lactose Monohydrate, NF, the disintegrant is Croscarmellose Sodium, NF, the binder is Povidone, USP, and the lubricant is Magnesium Stearate, NF.

In a further embodiment, modafinil comprises about 80% of the composition by weight, the diluent is a lactose monohydrate, which comprises about 8-15% of the composition by weight; the disintegrant is a cross-linked sodium carboxymethyl cellulose, which comprises about 1-10% of the composition by weight; the binder is polyvinyl pyrrolidone, which comprises about 1-10% of the composition by weight; and the binder is magnesium stearate, which comprises about 0.2-2.0% of the composition by weight. In certain more preferred embodiments, the diluent is Lactose Monohydrate, NF, and it can comprise about 9.5% of the composition by weight, the disintegrant is Croscarmellose Sodium, NF, and it can comprise about 5% of the composition by weight, the binder is Povidone, USP, and it can comprise about 5% of the composition by weight, and the lubricant is Magnesium Stearate, NF, and it can comprise about 0.5% of the composition by weight.

In other embodiments, modafinil comprises from about 90% of the composition by weight. Preferably the composition comprises a diluent, such as a lactose monohydrate, preferably from about 3-10% of the composition by weight; a disintegrant, such as a cross-linked sodium carboxymethyl cellulose, preferably from about 2-5% of the composition by weight; a binder such as a polyvinyl pyrrolidone, preferably from about 2-5% of the composition by weight; and a lubricant such as magnesium stearate, preferably from about 0.2-2.0% of the composition by weight. In certain more preferred embodiments, the diluent is Lactose Monohydrate, NF, and it can comprise about 3.5% of the composition by weight, the disintegrant is Croscarmellose Sodium, NF, and it can comprise about 3% of the composition by weight, the binder is Povidone, USP, and it can comprise about 3% of the composition by weight, and the lubricant is Magnesium Stearate, NF, and it can comprise about 1% of the composition by weight.

In yet another embodiment, the present invention provides for compositions of modafinil comprising 100 or 200 mg of modafinil, wherein the modafinil comprises from about 45-90% of the composition by weight. In other embodiments, modafinil comprises from about 60-90% or from about 70-80% of the composition.

In another embodiment, the compositions comprise one or more of a starch, such as corn starch; a lactose monohydrate; a microcrystalline cellulose; a pregelatinized starch; a cross-linked sodium carboxymethyl cellulose; a cross-linked sodium salt of a carboxymethyl ether of starch; a polyvinyl pyrrolidone, a hydroxypropyl methyl cellulose; a silicate salt, such as magnesium silicate; a salt of stearic acid, such as magnesium stearate; and a mineral salt, such as talc.

In an additional embodiment, the compositions comprise a lactose monohydrate, a corn starch, a cross-linked sodium carboxymethyl cellulose, a polyvinyl pyrrolidone, magnesium silicate, talc, and magnesium stearate.

In a further embodiment, the compositions comprise a lactose monohydrate, a microcrystalline cellulose, a pregelatinized starch, a cross-linked sodium carboxymethyl cellulose, a polyvinyl pyrrolidone, and magnesium stearate.

In another embodiment, the compositions comprise a lactose monohydrate, a cross-linked sodium carboxymethyl cellulose, a polyvinyl pyrrolidone, and magnesium stearate.

In certain preferred embodiments, the lactose monohydrate is Lactose Monohydrate, NF, or Fast Flo® #316; the microcrystalline cellulose is Microcrystalline cellulose, NF, or Avicel® PH 102; the pregelatinized starch is Pregelatinized Starch, NF, or Starch 1500®; the cross-linked sodium carboxymethyl cellulose is Croscarmellose Sodium, NF, or Ac-Di-Sol®; the polyvinyl pyrrolidone is Povidone K-29/32 or Povidone K90 D, USP and the magnesium stearate is Magnesium Stearate, NF.

In other embodiments, the compositions comprise at least one unit dose of modafinil. In a further embodiment, the compositions comprise one unit dose of modafinil. Preferably the unit dose is in a solid dose form, such as a tablet or capsule, and is more preferably is a tablet. In particular, the tablet can include 10, 25, 50 and preferably 100 mg of modafinil in a 250 mg tablet. In other embodiments, the tablet can include 200 mg of modafinil in a 500 mg tablet, 300 mg of modafinil in a 750 mg tablet, and 400 mg modafinil in 1000 mg tablet. In further embodiments, the tablet can include 100 mg of modafinil in a 125 mg tablet, 200 mg of modafinil in a 250 mg tablet, 300 mg of modafinil in a 375 mg tablet, and 400 mg in a 500 mg tablet. In other embodiments, the tablet can include 100 mg of modafinil in a 112 mg tablet, 200 mg of modafinil in a 224 mg tablet, 300 mg of modafinil in a 336 mg tablet, and 400 mg in a 448 mg tablet. Similarly, a capsule may contain 10, 25, 50, or 100 mg of modafinil in a 125 mg capsule, or 200 mg of modafinil in a 250 mg capsule. A capsule may also contain 100 mg of modafinil in a 112 mg capsule or 200 mg of modafinil in a 225 mg capsule.

In a second embodiment, the present invention provides for a process of preparing a solid dosage form of modafinil by wet mixing modafinil and excipients with water, drying and milling the granulated mixture. In certain embodiments, the final mixture is compressed into a tablet. In other embodiments, the final mixture is encapsulated. In particular, the process comprises the steps of:

(a) dry blending of modafinil and one or more excipients to form a dry mixture;
(b) wetting the dry mixture with water, preferably with purified water, to form a wet granulation mixture;
(c) drying the wet granulation mixture to form a dried granulation mixture;
(d) milling the dried granulation mixture to form a milled granulation mixture;
(e) mixing a lubricant in the milled granulation mixture to give a final blended mixture;
(f) preparing the final blended mixture in a solid dosage form suitable for oral administration.

In certain preferred embodiments, the final blended mixture is compressed into tablets. In other preferred embodiments, the final blended mixture is enclosed in a capsule.

Specifically, in step (a), modafinil is blended with all excipients in the final formulation, other than the lubricant. In particular, modafinil is thoroughly dry blended with the diluent(s), disintegrant(s) and binder to form a uniform dry mixture. Blenders appropriate for large scale dry blending include twin shell blenders, double cone blenders, and ribbon blenders. Ribbon blenders have the advantage of being used in continuous-production procedures. High-speed, high shear mixers may also be used and offer the advantage of shorter mixing times. The dry mixture may also be granulated, milled into a fine powder, passed through a mesh screen, or micronized, if necessary. Preferably, the dry blending was performed in high shear granulators.

The resulting dry mixture is then wetted with a wetting agent to form a wet granulation mixture in step (b). The wetting agent is typically added over time, usually from about 1 to about 15 minutes, with continuous mixing. Typically, the wetting agent is added to the blender used in the dry blending step. Preferably the wet granulation is carried out in a high shear granulator. In certain embodiments, the wetting agent is an aqueous-based solution. Preferably, the wetting agent is water without any additional solvents, and in particular, without organic solvents. More preferably, the water is purified water. The type and amount of wetting agent, rate of addition of wetting agent, and the mixing time influences the structure of the granules. The different types of granules, such as pendular, funicular, capillary, etc., can be manipulated to achieve the desired density, porosity, texture and dissolution pattern of the granules, which in turn, determines the compressibility, hardness, disintegration and consolidation characteristics of the dried mixture.

The wet granulation mixture is then dried in step (c) to form a dried granulation mixture with an appropriate moisture content. In certain embodiments, the drying means include a fluid bed or tray dryers. Fluid bed drying yield shorter drying times, in the range from 1 to 3 hours, while tray drying averages 10 to 13 hours. Preferably, the wet granulation mixture is dried in a fluid bed, for preferably about 1-3 hours. Fluid bed drying has the added advantages of better temperature control and decreased costs. The method of drying, drying time, and moisture content are critical to avoid decomposition, chemical migration, and other adverse physical characteristics of dried mixture which can affect the dosage form performance.

The dried granulation mixture is subsequently milled in step (d) to form a milled granulation mixture. The particle size of the dried granulation mixture is reduced to achieve an appropriate particle size distribution for the subsequent processes. In certain embodiments, milling is achieved using a high shear impact mill (such as Fitzpatrick) or a low shear screening mill (such as Comil). The dried granulation mixture may also be screened to select the desired granule size.

In the next step (e), the lubricant was blended with the dried granulation mixture to give a final blended mixture. In certain embodiments, a V blender or bin blenders are used. A preferred blender is a V-shell PK blender. A gentle blending is preferred, such that each granule covered with the lubricant, while minimizing the breaking up of the granules. Increased breaking of the granules results in fine powder, or "fines". A high fine content results in variations of weight and density during compression into a tablet, as well as increases the need for cleaning of the compression machinery.

The final blended mixture is then prepared in a solid dosage form suitable for oral administration. Solid dosage forms include tablets, capsules, pills, troches, cachets, and the like. In one embodiment, the final blended mixture is compressed into a tablet. The compression machinery typically contains two steel punches within a steel die cavity. The tablet is formed when pressure is exerted on the dried granulation mixture by the punches in the cavity, or cell. Tableting machines include single-punch machines, rotary tablet machines, gravity feed, and powder assisted machines. Preferably, gravity feed or powder assisted machines are used. Rotary machines operating at high speeds suitable for large-scale production include double rotary machines and single rotary machines. Tablets can also include sugar-coated tablets, film-coated tablets, enteric-coated tablets, multiple-compressed tablets, controlled-release tablets, tablets for solution, effervescent tablets or buccal and sublingual tablets.

Compressed tablets may be characterized by a number of specifications, including diameter size, shape, thickness, weight, hardness, friability, disintegration time, and dissolution characteristics. The compositions of the current invention preferably have similar properties to that of Provigil®. The tablets preferably have weights, friability and dissolution rates in accordance with USP standards. The preferred hardness and thickness ranges of various sized tablets are shown below in Table 1:

| Amount of Modafinil (mg) | Hardness (Kp) | Thickness (inches) |
| --- | --- | --- |
| 100 | 4-14 | 0.132-0.171 |
| 200 | 7-21 | 0.163-0.219 |
| 300 | 9-22 | 0.197-0.248 |
| 400 | 10-22 | 0.268-0.249 |

In another embodiment, the final blended mixture is enclosed in capsules, preferably hard gelatin capsules. The hard gelatin capsules are commercially available, and are generally made from gelatin, colorants, optionally an opacifying agent such as titanium dioxide, and typically contain 12-16% water. The hard capsules can be prepared by filling the longer end of the capsule with the final blended mixture, and slipping a cap over the top using mG2, Zanasi, or Höfliger and Karg (H&K) machines.

In an alternative embodiment, the present invention provides for a process of preparing a solid dose form of modafinil by dry mixing modafinil with the excipients. In certain embodiments, the mixture is compressed into a tablet. In other embodiments, the mixture is encapsulated. In particular, the process comprises the steps of:

(a) dry blending of modafinil and one or more excipients to form a dry mixture;
(b) mixing a lubricant in the dry mixture to give a final blended mixture;
(c) preparing the final blended mixture in a solid dosage form suitable for oral administration.

In certain preferred embodiments, the final blended mixture is compressed into tablets. In other preferred embodiments, the final blended mixture is enclosed in a capsule.

Specifically, in step (a), modafinil is blended with all excipients in the final formulation, other than the lubricant. Preferably, modafinil is thoroughly dry blended with the diluent(s), disintegrant(s) and a binder to form a uniform dry mixture. Blenders appropriate for large scale dry blending include twin shell blenders, double cone blenders, V blenders or bin blenders. A preferred blender is a V-shell PK blender. High-speed, high shear mixers may also be used. The dry mixture may also be granulated, milled into a fine powder, passed through a mesh screen, or micronized, if necessary.

In the next step (b), the lubricant was blended with the dry mixture to give a final blended mixture. In certain embodiments, a V blender or bin blenders are used. A preferred blender is a V-shell PK blender.

The final blended mixture is then prepared in a solid dosage form suitable for oral administration. Solid dosage forms include tablets, capsules, pills, troches, cachets, and the like. In one embodiment, the final blended mixture is compressed into a tablet. In another embodiment, the final blended mixture is enclosed in capsules, preferably hard gelatin capsules.

Other aspects of the invention also include use of these compositions for the treatment of a disease or disorder in a subject in need thereof comprising administering to the subject a therapeutically effective amount of the compositions of the present invention. In particular, the present compositions are useful in the treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder and fatigue, and improvement of cognitive dysfunction.

EXAMPLES

The materials, methods, and examples presented herein are intended to be illustrative, and not to be construed as limiting the scope or content of the invention. Unless otherwise defined, all technical and scientific terms are intended to have their art-recognized meanings.

Example 1

Formulation of a 100 mg Modafinil Tablet

| Components | Amount per tablet (mg) |
|---|---|
| Modafinil | 100.0 |
| Lactose Monohydrate, NF (Fast Flo #316) | 71.75 |
| Microcrystalline Cellulose, NF (Avicel PH 102) | 26.0 |
| Pregelatinized Starch, NF (Starch 1500) | 27.25 |
| Povidone K29/32, USP | 13.0 |
| Croscarmellose Sodium, NF (Ac-Di-Sol) | 10.0 |
| Magnesium Stearate, NF | 2.0 |
| Total Tablet Weight | 250.0 |

Example 2

Formulation of a 200 mg Modafinil Tablet

| Components | Amount per tablet (mg) |
|---|---|
| Modafinil | 200.0 |
| Lactose Monohydrate, NF (Fast Flo #316) | 143.5 |
| Microcrystalline Cellulose, NF (Avicel PH 102) | 52.0 |
| Pregelatinized Starch, NF (Starch 1500) | 54.5 |
| Povidone K29/32, USP | 26.0 |
| Croscarmellose Sodium, NF (Ac-Di-Sol) | 20.0 |
| Magnesium Stearate, NF | 4.0 |
| Total Tablet Weight | 500.0 |

Example 3

Large Scale Preparation (250 kg) of Modafinil Formulation

Step (a): Dry Mixture

Pass Modafinil (100.00 kg), Lactose Monohydrate NF (71.75 kg), Pregelatinized Starch NF (27.25 kg), Microcrystalline Cellulose NF (26.00 kg), Croscarmellose Sodium NF (10.00 kg) and Povidone K29/32 USP (13.00 kg) through a #10 mesh screen. Add the screened material to a 600 liter Collette mixer. Mix for 6 minutes at low speed, without a chopper.

Step (b): Wet Granulation Mixture

To a stainless steel tank, add Purified Water USP (100.00 kg). While mixing the dry mixture at low speed, pump the purified water into the Collette mixer at a rate of 14 kg/min. After the water has been added, continue to mix the wet granulation mixture at low speed and low chopper for 30 additional seconds. Additional mixing, and/or additional water may be required to achieve the desired consistency. Discharge the wet granulation mixture from the Collette bowl into a suitable transport vessel.

Step (c): Drying Wet Granulation Mixture

Spread the wet granulation evenly, and not to exceed 2 inches in depth, on 2 drying racks lined with 40 lb. Kraft paper. Place the racks in G&G Steam Heated Oven. Dry the wet granulation mixture at 60° C.±2° C. until a L.O.D. of 1.0-2.1% is reached.

Step (d): Milling the Dried Granulation Mixture

Pass the dried granulation mixture through an auger feed Fitz®mill (Model DAS06), with knives forward, at medium speed, through a 2A screen.

Step (e): Mixing a Lubricant

Add the dried granulation mixture from the previous step to a 20-cubic foot V-shell PK blender (Model C266200). Pass Magnesium Stearate NF (2.00 kg) through a 10-mesh screen into a properly prepared container. Add approximately half of the Magnesium Stearate to each side of the PK blender and blend for 5 minutes.

Step (f): Compression into Tablets

Add the blended granulation mixture form the previous step to a Kikusui tablet press for compression into capsule-shaped tablets. The compression equipment can be outfitted to make tooling for a 100 mg tablet (0.496×0.218 inches), a 200 mg tablet (0.625×0.275 inches, bisected), 300 mg tablet (0.715×0.315 inches) and a 400 mg tablet (0.750×0.330 inches).

Alternative Step (f): Filling into Capsules

Add the blended granulation mixture form the previous step to H & K 400 machine for filling the appropriate size capsules.

Example 4

Formulation of Modafinil Capsules

| Components | Amount per capsule (mg) | | | | |
|---|---|---|---|---|---|
| Modafinil | 12.5 | 25.0 | 50.0 | 100.0 | 200.0 |
| Lactose Monohydrate, NF | 99.38 | 86.88 | 61.88 | 11.88 | 23.75 |
| Povidone K90 D, USP | 6.25 | 6.25 | 6.25 | 6.25 | 12.5 |
| Croscarmellose Sodium, NF (Ac-Di-Sol ®) | 6.25 | 6.25 | 6.25 | 6.25 | 12.5 |
| Magnesium Stearate, NF | 0.625 | 0.625 | 0.625 | 0.625 | 1.25 |
| Total Capsule Weight | 125.0 | 125.0 | 125.0 | 125.0 | 250.0 |

Example 5

Formulations of High Dose Modafinil

| Components | Amount (mg) | | |
|---|---|---|---|
| Modafinil | 99.79 | 100.0 | 200.0 |
| Lactose Monohydrate, NF | 12.47 | 4.2 | 8.4 |
| Povidone K90 D, USP | 6.24 | 3.46 | 6.92 |
| Croscarmellose Sodium, NF (Ac-Di-Sol ®) | 6.24 | 3.46 | 6.92 |
| Magnesium Stearate, NF | 1.26 | 1.12 | 2.24 |
| Total Weight | 126.0 | 112.2 | 224.5 |

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended claims cover all equivalent variations as fall within the scope of the invention.

What is claimed is:

1. A composition comprising modafinil, wherein modafinil comprises about 90% by weight of the composition; a lactose monohydrate, which comprises about 3-10% of the composition by weight; a cross-linked sodium carboxymethyl cellulose, which comprises about 2-5% of the composition by weight; a polyvinyl pyrrolidone, which comprises about 2-5% of the composition by weight; and magnesium stearate, which comprises about 0.2-2.0% of the composition by weight.

2. The composition of claim 1, wherein modafinil is the levorotatory isomer of modafinil.

3. A composition comprising modafinil, wherein modafinil comprises 70-80% of the composition by weight; a lactose monohydrate from about 3-20% of the composition by weight; a cross-linked sodium carboxymethyl cellulose from about 2-10% of the composition by weight; a polyvinyl pyrrolidone from about 2-10% of the composition by weight, and magnesium stearate from about 0.2-2.0% of the composition by weight.

4. The composition of claim 3, wherein modafinil is the levorotatory isomer of modafinil.

* * * * *